(12) United States Patent
Fitzhugh et al.

(10) Patent No.: US 7,226,586 B2
(45) Date of Patent: Jun. 5, 2007

(54) HIGHLY CROSS-LINKED, EXTREMELY HYDROPHOBIC NITRIC OXIDE-RELEASING POLYMERS AND METHODS FOR THEIR MANUFACTURE AND USE

(75) Inventors: Anthony L. Fitzhugh, Frederick, MD (US); Robert Cafferata, Santa Rosa, CA (US); Larry K. Keefer, Bethesda, MD (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 90 days.

(21) Appl. No.: 10/623,239

(22) Filed: Jul. 17, 2003
(Under 37 CFR 1.47)

(65) Prior Publication Data

US 2005/0079148 A1    Apr. 14, 2005

Related U.S. Application Data

(62) Division of application No. 09/972,219, filed on Oct. 4, 2001, now Pat. No. 6,703,046.

(51) Int. Cl.
| | | |
|---|---|---|
| A61K 31/785 | (2006.01) | |
| A61K 9/14 | (2006.01) | |
| A61K 33/08 | (2006.01) | |
| A61K 31/765 | (2006.01) | |
| A61F 2/00 | (2006.01) | |

(52) U.S. Cl. .................. 424/78.27; 424/484; 424/423; 424/718

(58) Field of Classification Search ................ 424/484, 424/422, 423, 718, 78.27, 400; 525/540
See application file for complete search history.

(56) References Cited

U.S. PATENT DOCUMENTS

| | | | |
|---|---|---|---|
| 4,954,526 A | 9/1990 | Keefer | |
| 5,039,705 A | 8/1991 | Keefer et al. | |
| 5,155,137 A | 10/1992 | Keefer et al. | |
| 5,171,217 A | 12/1992 | March et al. | |
| 5,212,204 A | 5/1993 | Keefer et al. | |
| 5,229,172 A | 7/1993 | Cahalan et al. | |
| 5,250,550 A | 10/1993 | Keefer et al. | |
| 5,268,465 A | 12/1993 | Bredt et al. | |
| 5,366,997 A | 11/1994 | Keefer et al. | |
| 5,380,758 A | 1/1995 | Stamler et al. | |
| 5,405,919 A | 4/1995 | Keefer et al. | |
| 5,428,070 A | 6/1995 | Cooke et al. | |
| 5,468,630 A | 11/1995 | Billiar et al. | |
| 5,482,925 A | 1/1996 | Hutsell | |
| 5,519,020 A | 5/1996 | Smith et al. | |
| 5,525,357 A | 6/1996 | Keefer et al. | |
| 5,574,068 A | 11/1996 | Stamler et al. | |
| 5,583,101 A | 12/1996 | Stamler et al. | |
| 5,632,981 A | 5/1997 | Saavedra et al. | |
| 5,650,447 A | 7/1997 | Keefer et al. | |
| 5,658,565 A | 8/1997 | Billiar et al. | |
| 5,676,963 A * | 10/1997 | Keefer et al. ................ | 424/423 |
| 5,683,668 A | 11/1997 | Hrabie et al. | |
| 5,691,423 A | 11/1997 | Smith et al. | |
| 5,700,830 A | 12/1997 | Korthuis et al. | |
| 5,714,511 A | 2/1998 | Saavedra et al. | |
| 5,718,892 A | 2/1998 | Keefer et al. | |
| 5,721,365 A | 2/1998 | Keefer et al. | |
| 5,770,645 A | 6/1998 | Stamler et al. | |
| 5,789,447 A | 8/1998 | Wink, Jr. et al. | |
| 5,814,656 A | 9/1998 | Saavedra et al. | |
| 5,814,667 A | 9/1998 | Mitchell et al. | |
| 5,837,313 A | 11/1998 | Ding et al. | |
| 5,837,736 A | 11/1998 | Mitchell et al. | |
| 5,840,759 A | 11/1998 | Mitchell et al. | |
| 5,877,216 A | 3/1999 | Place et al. | |
| 5,891,459 A | 4/1999 | Cooke et al. | |
| 5,910,316 A | 6/1999 | Keefer et al. | |
| 5,945,452 A | 8/1999 | Cooke et al. | |
| 5,958,427 A | 9/1999 | Salzman et al. | |
| 5,962,520 A | 10/1999 | Smith et al. | |
| 5,994,444 A * | 11/1999 | Trescony et al. ........... | 524/429 |
| 6,024,918 A | 2/2000 | Hendriks et al. | |
| 6,703,046 B2 * | 3/2004 | Fitzhugh et al. ............ | 424/423 |

FOREIGN PATENT DOCUMENTS

| | | |
|---|---|---|
| WO | WO 00/02501 | 1/2000 |
| WO | WO 0030658 A1 | 6/2000 |

OTHER PUBLICATIONS

Pulfer et al. (Incorporation of Nitric Oxide-Releasing Crosslinked polyethyleneimine Microspheres Into Vascular Grafts; Journal of Biomedical Materials Research; Wiley, New York, NY, vol. 37, No. 2, Nov. 1997; pp. 182-189).*

Bauer et al.; Evaluation of Linear Polyethyleneimine/nitric Oxide Adduct on Wound Repair: Therapy versus Toxicity; Wound Repair & Regeneration, Nov./Dec. 1998, pp. 569/577.

Chandy et al; "Use of Plasma Glow for Surface/Engineering Biomolecules to Enhance Bloodcompatibility of Dacron and PTFE Vascular Prosthesis." Biomaterials 21:699-712.

Drago; "Free Radicals in Inorganic Chemistry." No. 36, Advances in Chemistry Series, American chemical society, Washington, D. C. 1962, pp. 143/149.

(Continued)

*Primary Examiner*—Michael G. Hartley
*Assistant Examiner*—Blessing Fubara

(57) ABSTRACT

Extremely hydrophobic nitric oxide (NO) releasing polymers are disclosed. The extremely hydrophobic NO-releasing polymers provided are extensively cross-linked polyamine-derivatized divinylbenzene diazeniumdiolates. These polymers can be loaded with extremely high NO levels and designed to release NO in manners than mimic natural biological systems. The NO-releasing extremely hydrophobic polymers provided can maintain a sustained NO release for periods exceeding nine months. Also provided are related medical devices made using these NO-releasing extremely hydrophobic polymers.

13 Claims, No Drawings

OTHER PUBLICATIONS

Hanson et al; Nitric Oxide Donors: A Continuing Opportunity in Drug Design; Advances in Pharmacology, vol. 34, pp. 383/398.

Hrabie et al; "New Nitric Oxide/Releasing Zwitterions Derived from Polyamines." J. Org. Chem. 1993, 58, 1472/1476.

Jordi; Jordi Gel Columns for Size Exclusion Chromatography; Column Handbook for Size Exclusion Chromatography; 1999, pp. 367/425.

Kaul et al.; Polymeric/Based Perivascular Delivery of a Nitric Oxide Donor Inhibits Intimal Thicening After Balloon Denudation Arterial Injury: Role of Nuclear Factor/kappaB; Journal of the Americna College of Cardiology, vol. 35, No. 2, 2000:493/501.

Keefer et al; "NONOates" (1/Substituted Diazen/I/ium/1,2/diolates) as Nitric Oxide Donors: Convenient Nitric Oxide Dosage Forms. Methods in Enzymology, vol. 268: 281/293.

Mowery et al.; Preparation and Characterization of Hydrophobic Polymeric Films That Are Thromboresistant Via Nitric Oxide Release; Biomaterials 21 (2000) 9/21.

Saavedra et al.; "Conversion of Polysaccharide to Nitric Oxide/Releasing Form Dual/Mechanism Anticoagulant Activity of Diaseniumdiolated Heparin." Bioorganic & Medicinal Chemistry Letter 10 (2000) 1/3.

Smith et al.; Nitric Oxide/Releasing Polymers Containing the [N(O)NO]Group; J. Med. Chem. 1996, 39, 1148/1156.

Downey et al.; Growth Mechanism of Poly(divinylbenzene) Microspheres in Precipitation Polymerization; American Chemical Society, Easton, US, vol. 32, No. 4, May 4, 1999; pp. 2838-2844.

Pulfer et al.; Incorporation of Nitric Oxide-Releasing Crosslinked Polyethyleneimine Microspheres Into Vascular Grafts; Journal of Biomedical Materials Research; Wiley, New York, NY, vol. 37, No. 2, Nov. 1997; pp. 182-189.

Zhang et al.; Synthesis of Nitric Oxide Releasing Silicone Rubbers for Biomedical Applications; Polymer Preprints; vol. 40, No. 2, 1999, pp. 799-800.

\* cited by examiner

HIGHLY CROSS-LINKED, EXTREMELY HYDROPHOBIC NITRIC OXIDE-RELEASING POLYMERS AND METHODS FOR THEIR MANUFACTURE AND USE

RELATED APPLICATIONS

This application is a divisional application of U.S. patent application Ser. No. 09/972,219 filed Oct. 4, 2001 now U.S. Pat. No. 6,703,046, the contents of which are incorporated herein by reference.

FIELD OF THE INVENTION

The present invention generally provides for methods of preparing nitric oxide releasing highly cross-linked, extremely hydrophobic polymers. The present invention relates to highly cross-linked, extremely hydrophobic polymers capable of providing prolonged release of nitric oxide under physiological conditions. Specifically, the present invention relates to the use of highly cross-linked, extremely hydrophobic polymers as therapeutic agents. More specifically, the present invention is directed at medical devices made from nitric oxide-releasing highly cross-linked, extremely hydrophobic polymers.

BACKGROUND OF THE INVENTION

Nitric oxide (NO) is a simple diatomic molecule that is a powerful signaling compound and cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOS1, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{+2}$ levels. Increased intracellular $Ca^{+2}$ concentrations result in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Nitric oxide's therapeutic potential has been studied in a diverse number of clinical indications including cancer, coronary artery heart disease, restenosis, hypertension, angiogenesis, and sexual dysfunction. Moreover, recent studies have demonstrated that NO also possesses considerable in vivo and ex vivo antimicrobial activity (Fang, F. C., 1997. Perspectives series: host/pathogen interactions. Mechanisms of Nitric Oxide-antimicrobial activity. J Clin Invest Jun. 15; 99 (12):2818-25; Fang, F. C., 1999. Nitric Oxide and Infection, Kluwer Academic/Plenum Publishers: New York; see also: U.S. Pat. No. 5,814,666 [the "'666 patent"] filed Apr. 24, 1995 and issued to Green at al.; the entire contents of both are hereby incorporated by reference) and is thus suitable for use in the treatment of infectious diseases.

Nitric oxide's unique combination of physiological properties has made it an ideal candidate for treating vascular diseases, specifically ischemic heart disease. Ischemic heart disease results when blood flow to the heart is restricted, usually as a result of a blockage in the one or more coronary arteries. Most forms of ischemic heart disease are treated using coronary artery bypass graft (CABG) surgery or by restoring blocked vessel patency using transluminal coronary angioplasty (PTCA) and/or stent placement.

However, CABG and PTCA can fail due to restenosis, a multi-factorial process whereby the previously opened vessel lumen narrows and becomes re-occluded. Restenosis has been found to occur in approximately 30% to 50% of angioplasty and other transcatheter patients within three to six months (Currier, J. W. et al. 1995. Restenosis after percutaneous transluminal coronary angioplasty: have we been aiming at the wrong target? J Am Coll Cardiol; 25:516-520). Restenosis is initiated when thrombocytes (platelets) adhere to a vessel injury site caused by balloon inflation and initiate thrombogenesis (clot formation) and/or vascular smooth muscle cell over-proliferation (hyperplasia). As a result, the previously opened lumen begins to narrow, restricting or occluding the injured vessel. Recently, researchers have demonstrated that the anti-thromobogenic and anti-smooth muscle proliferative effects of NO can significantly reduce restenosis in animals (Bohl, K. S. et al. 2000. Nitric oxide-generating polymers reduce platelet adhesion and smooth muscle cell proliferation. Biomaterials; 21(22): 2273-8; Buergler, J. M. et al. Use of nitric-oxide-eluting polymer-coated stents for prevention of restenosis in pigs. Coron. Artery Dis.; 11(4): 351-7; Janero, D. R. et al. Nitric oxide and postangioplasty restenosis: pathological correlates and therapeutic potential. 29(12): 1199-221; Le Tourneau, T. et al. J. Am. Coll. Cardiol. Role of nitric oxide in restenosis after experimental balloon angioplasty in the hypercholesterolemic rabbit: effects on neointimal hyperplasia and vascular remodeling. 33 (3): 876-82). Consequently, significant interest has been directed at developing medical devices that focus the anti-restenotic effects of NO directly on anatomical sites at greatest risk for restenosis.

Another method for treating an ischemic organ, especially the heart, is to revascularize the affected area by inducing the growth of new blood vessel and capillaries. This process, called angiogenesis, has received considerable attention as an alternative to CABG and PTCA for the treatment of ischemic heart disease (Dulak, J. et al., 2000. Nitric oxide induces the synthesis of vascular endothelial growth factor by rat vascular smooth muscle cells. *Arterioscler Thromb Vasc Biol*; March;20(3): 659-666). Compounds shown to induce or up-regulate angiogenesis include nitric oxide, fibroblast growth factor (FGF) vascular endothelial growth factor (VEGF) and members of the epidermal growth factor (EGF) family such as transforming growth factor alpha (TGF alpha), transforming growth factor beta (TGF beta), betacellulin, amphiregulin, and vaccinia growth factor among other factors. Nitric oxide is involved in the regulation of these biochemicals; therefore under certain conditions NO may exert angiogenic effects.

The in vivo use of NO-releasing compounds to induce angiogenesis, prevent restenosis, reduce unwanted thrombogenicity, and promote wound healing appears to be promising. However, the current NO-releasing techniques have failed to fully mimic the natural NO release associated with endothelial cells. As previously mentioned, natural NO production is regulated by a combination of constitutive and inducible enzymes. Endothelial cells, the primary regulator of vascular homeostasis, are provided with continuous low levels of NO release through constitutive enzyme (eNOS) activity. Moreover, when required, inducible enzymes (iNOS) can provide cells with momentary bursts of NO. In principle, such transient physiological bursts of NO can be mimicked using polymers or metallic surfaces coated with NO-donating materials that release NO immediately upon exposure to aqueous physiological environments. However, the sustained delivery of low levels of NO by endothelial cells has proven to be much more difficult to simulate with NO-releasing materials.

Another daunting task has proven to be the preferential or selective delivery of NO to specific target organs. Nitric oxide reacts readily with a variety of biomolecules and can be toxic when administered systemically. Previous efforts to provide therapeutic NO levels have generally relied on NO prodrugs such as glyceryl trinitrate and sodium nitroprusside. These compounds, unlike NO gas, are generally stable; however, their pharmacological activity is usually short lived. Moreover, the enzymes and co-factors necessary to convert glyceryl trinitrate into NO are rapidly depleted. Hence, repeated use of this compound over short time periods results in the development of drug tolerance. Prolonged use of sodium nitroprusside can lead to the excessive generation of highly toxic cyanide which can accumulate as a result thus limiting its long-term use. Consequently, significant attention has been directed towards the development of NO generators or donor compounds that can be used for the sustained localized therapeutic administration of NO without toxic side effects.

Nitric oxide-releasing compounds suitable for in vivo applications have been developed by a number of investigators. As early as 1960 it was demonstrated that nitric oxide gas could be reacted with amines to form NO-releasing anions having the following general formula:

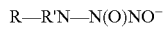

Formula 1

Salts of these compounds spontaneously decompose and release NO in solution. (R. S. Drago et al J. Am. Chem. Soc. 1960, 82, 96-98.)

Nitric oxide-releasing compounds with sufficient stability in aqueous physiological buffers to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and in J. A. Hrabie et al, J. Org. Chem. 1993, 58, 1472-1476, all of which are herein incorporated by reference. Briefly, Hrabie et al. describes NO-releasing intramolecular salts (zwitterions) having the general formula:

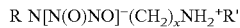

Formula 2

Stable NO-releasing compounds of Formula 2 (nitric oxide/nucleophile complexes) have been coupled to a wide range of amine containing polymers whose backbone molecular structure is non- or poorly cross-linked (Smith D. J. et al. 1996 Nitric oxide-releasing polymers containing the [N(O)NO]⁻ group. J Med Chem 39:1148-1156, Pulfer, S. K. et al. 1997 Incorporation of nitric oxide-releasing crosslinked polyethyleneimine microspheres into vascular graft. J. Biomed Mater Res. 37:182-9, Mowery, K. A. et al. 2000. Preparation and characterization of hydrophobic polymeric films that are thromboresistant via nitric oxide release. Biomaterials 21:9-21, Bauer, J. A. et al. 1998. Evaluation of linear polyethyleneimine/nitric oxide adduct on wound repair:therapy verses toxicity. Wound Repair and Regeneration, Vol. 6 No. 6:569-576. The[N(O)NO]⁻ (abbreviated herein after at NONO) containing compounds thus described release NO via a first order reaction that is predictable and easily quantified. Such NO-donor compounds are commonly known in the art as diazeniumdiolates.

U.S. Pat. No. 5,405,919 ("the '919 patent") is an example of a patent that describes methods for bonding or coupling diazeniumdiolate NO-releasing groups to biologically acceptable polymers. Examples of such polymers include polyolefins, such as polystyrene, polypropylene, polyethylene, polyterafluoroethylene, polyvinylidene, or derivatized polyolefins such as polyethyleneimine, polyesters, polyethers, polyurethanes and the like. The NO-release totals for the polymers cited in the '919 patent were measured in the range of 3 to 11 nmol/mg. Implantable medical devices composed of biologically acceptable forms of such polymers represent a potential means for the site-specific NO delivery to a particular tissue or target organ.

Significant progress has been made in the preparation, formulation, and protective group derivatization of diazeniumdiolated amines. U.S. Pat. No. 5,155,137 discloses general methods of preparing polyamine/nitric oxide complexes suitable for treating cardiovascular diseases. The '666 patent describes a novel means of formulating a diazeniumdiolated amine by impregnating such moieties in multilamellar liposomes. Liposome encapsulated diazeniumdiolates are shielded from the aqueous milieu until phagocytized by a macrophage. Once inside the macrophage, the liposome encapsulated diazeniumdiolate releases its contents into the lumen of the phagolysome and there is a corresponding generation of NO as the "free" diazeniumdiolate moieties. In vitro studies have shown that the method described in the '666 patent is a particularly effective means of killing phagocytized pathogenic microorganisms within macrophages. Liposome encapsulation of diazeniumdiolates appears to function entirely as a means of enhancing the delivery of such compounds to cells as there is no corresponding extension in the half-life of NO release vs. non-encapsulated diazeniumdiolates.

U.S. Pat. No. 5,366,997 discloses techniques by which the distal oxygen atom of the diazeniumdiolate anion can be derivatized through the covalent attachment of a protective group. Such modified diazeniumdiolates are generally quite stable when exposed to aqueous buffers under conditions of physiological temperature and pH. However, certain organs are able to metabolically remove the protective group from protected diazeniumdiolates with the concomitant formation of the parent diazeniumdiolate moiety.

The availability of stable NO-releasing diazeniumdiolates has greatly advanced the potential for developing NO-delivering medicaments. However, there is still a need for even better control over the duration of in vivo NO release. Specifically, there is a need to develop NO-donating polymeric materials that are capable of sustained NO release in physiological buffer solutions for periods lasting several months to years. Moreover, there is a need to develop materials that can better mimic in situ NO production where NO bursts are followed by sustained lower level release of NO delivered directly to a target organ or group of cells.

SUMMARY OF THE INVENTION

It is an object of the present invention to provide highly cross-linked, extremely hydrophobic polymers capable of the sustained release of nitric oxide over long periods.

It is another object of the present invention to provide highly cross-linked, extremely hydrophobic nitric oxide-releasing polymers that are biocompatible.

It is another object of the present invention to provide highly cross-linked, extremely hydrophobic nitric oxide-releasing polymers that are biocompatible and in the form of micro-beads.

It is another object of the present invention to provide highly cross-linked, extremely hydrophobic nitric oxide-releasing polymers that are biocompatible and useful as a therapeutic agent.

It is another object of the present invention to provide medical devices made using highly cross-linked, extremely hydrophobic, nitric oxide-releasing polymers that are biocompatible and provide for the localized delivery of nitric oxide in sustained therapeutic levels to target organs or groups of cells.

The present invention discloses methods of producing polymers capable of releasing nitric oxide (NO) at therapeutic levels for surprisingly prolonged periods. The polymers of the present invention are generally comprised of diazeniumdiolated forms of polyamine functionalized divinylbenzene. Most preferably, the polymers of the present invention are diazeniumdiolated polyethyleneimine derivatized forms of divinylbenzene. Unlike the prior art, the diazeniumdiolated polyamines of the present invention are covalently linked to a backbone molecular structure that is highly cross-linked and extremely hydrophobic. The polymers of the present invention can be formed into micro-beads, amorphous masses, or cast into specific shapes.

As is known generally in the prior art for NO-releasing agents, the polymers of the present invention can be used to treat or prevent a wide range of conditions including, but not limited to, ischemic heart disease, restenosis, cancer, hypertension, infectious diseases and sexual dysfunction. Moreover, polymers of the present invention can be used to promote the growth of new blood vessels and capillaries in a process known as angiogenesis. The NO-releasing polymers of the present invention may also be used to reduce inflammation and promote healing when used as a coating or substrate for implantable medical devices and materials including, but not limited to, stents, vascular grafts, pacemaker leads, heart valves, electrodes, sensors, trocars, guide wires, catheters, penile implants, condoms, tampons, sanitary napkins, ocular lenses, sling materials, sutures, wound dressings/bandages, blood collection bags and storage tubes, tubing used for blood transfusions and hemodialysis, and the like.

The NO-releasing highly cross-linked, extremely hydrophobic polymers of the present invention can also be co-polymerized or blended with other biocompatible polymers such as, but not limited to, polyvinylchloride, polystyrene, poly-L-lactides/glycolides, polycaprolactone, polyglycols and the like. Moreover, NO-releasing polymeric micro-beads of the present invention can be administered directly to a target organ or group of cells. For example, the NO-releasing diazeniumdiolated micro-beads made in accordance with the teachings of the present invention can be injected via a catheter directly into the arteries of the heart and allowed to disseminate until they become lodged in the coronary micro-vasculature. The polymeric micro-beads of the present invention are generally less than 5 μm in diameter and their migration will be stopped when they encounter vessels that are narrower than the diameter of the beads. Once the vessels are occluded, NO from the micro-beads is continuously released in an amount sufficient to induce angiogenesis at the site of blockage. By such a process, the NO-releasing micro-beads will initiate the development of new blood vessels around the site of vascular occlusion. In another embodiment, sustained local levels of NO can be generated by directly injecting micro-beads into the pericardial sac via a catheter.

In yet another embodiment, the highly cross-linked, extremely hydrophobic NO-releasing polymers of the present invention can be incorporated into or on the surface of a vascular stent. The sustained NO release provided by the diazeniumdiolated polymers of the present invention will prevent restenosis by inhibiting endothelial cell hyperplasia at or near the stent site. Moreover, the NO-releasing stent made in accordance with the teachings of the present invention will also inhibit thrombus formation and platelet activation in the vicinity of the device.

In summary, the highly cross-linked, extremely hydrophobic NO-releasing polymers of the present invention provide compounds that have surprisingly high NO loading capacities and an equally surprisingly long duration of NO release when immersed in aqueous physiological buffer solutions. The highly cross-linked, extremely hydrophobic NO-releasing polymers of the present invention release NO for periods exceeding nine months. By comparison with the prior art, as described in U.S. Pat. No. 5,405,919, the present invention results in increases of several orders of magnitude in terms of the quantity and period of sustained NO release. Moreover, the present invention also allows for methods of controlling NO load as well as final polymer geometry. This combination of properties enables those skilled in the art of polymer science and chemistry to design NO-releasing therapeutics and medical devices capable of delivering highly predictable doses of NO for long periods and localized to discrete anatomical sites.

DETAILED DESCRIPTION OF THE INVENTION

Nitric oxide's diverse role as a bioregulatory agent has stimulated significant interest in the biological and medical sciences. Numerous approaches have been developed in an effort to provide safe and effective methods for administering NO to mammals including humans. Exogenous NO sources such as pure NO gas are highly toxic, short lived and relatively insoluble in physiological fluids. Consequently, the systemic delivery of exogenous NO is generally accomplished using organic nitrate prodrugs such as nitroglycerin tablets, intravenous suspensions, sprays and transdermal patches. The human body rapidly converts nitroglycerin and other NO prodrugs into NO; however, on repeated use the enzyme levels and co-factors required to activate the prodrug are depleted. Consequently, drug tolerance results in 10 to 12 hour physiological recovery intervals before organic nitrate administration will again elevate serum NO levels.

One potential method for overcoming the disadvantages associated with NO prodrug administration is to provide NO-releasing therapeutics that do not require activation by endogenous enzyme systems. Early efforts to provide NO-releasing compounds suitable for in vivo use were described in U.S. Pat. No. 4,954,526 issued to Keefer et al. Sep. 4, 1990. The '526 patent disclosed diazeniumdiolated primary amines salts having the general formula:

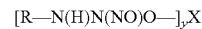
[R—N(H)N(NO)O—]$_y$X   Formula 3 wherein R is a lower alkyl, aryl, arylalkyl or cycloalkyl, any of which R groups may be substituted by one to three functional groups selected from the group consisting of halo, hydroxyl, alkoxy, amino, amido, formyl, carboxyl, or nitro; and wherein X is a pharmacologically acceptable cation, metal center, or organic group selected from lower alkyl, acyl, or amino and y is 1 to 3 consistent with the valence of X. Many of these compounds were known when the '526 patent was filed, however, their biological properties were not and the '526 patent is considered a pioneering patent in the field of medicinal NO chemistry.

Another important group of NO-releasing compounds are described in U.S. Pat. Nos. 5,380,758, 5,574,068, 5,583,101, 5,593,876 and 5,770,645. These patents disclose S-nitrosothiols having the general formulae:

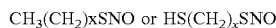

wherein: X equals 2 to 20; and

wherein: X equals 2 to 20 and Y is selected from the group consisting of fluoro, $C_1$-$C_6$ alkoxy, cyano, carboxamido, $C_3$-$C_6$ cycloalkyl, aralkoxy, $C_2$-$C_6$ alkylsulfinyl, arylthio, $C_1$-$C_6$ alkylamino, $C_2$-$C_{15}$ dialkylamino, hydroxy, carbamoyl, $C_1$-$C_6$ N-alkylcarbamoyl, $C_2$-$C_{15}$ N,N-dialkylcarbamoyl, amino, hydroxyl, carboxyl, hydrogen, nitro and aryl; wherein aryl includes benzyl, naphthyl, and anthracenyl groups. However, the nitrosothiol→NO reactions are kinetically complicated and difficult to control and therefore not as ideally suited for medicaments as the clean first order kinetics associated with the diazeniumdiolates.

The general method for diazeniumdiolating amines used in the present invention as originally developed by R. S. Drago et al.; however, some of these compounds were unstable at temperatures above −78° C. and consequently not suited for formulating in vivo medications requiring long-term room temperature stability (Drago et al. 1960. The reaction of nitrogen(II) with various primary and secondary amines. J. Am. Chem. Soc. 1819-1822, the entire contents of which is hereby incorporated by reference).

NO-releasing compounds having sufficient stability to be formulated into pharmaceutical preparations are disclosed in U.S. Pat. No. 4,954,526 (the '526 patent). However, the primary amine derivatives of the '526 patent were highly reactive and the ability to control the NO release rates from these compounds was limited. In an effort to provide a more easily controlled release of NO and therefore improve their medical utility, Keefer et al. developed methods for diazeniumdiolating secondary amines as disclosed in U.S. Pat. No. 5,039,705 (the '705 patent). The '705 patent describes diazeniumdiolated secondary amines having the following general structure:

Formula 4:

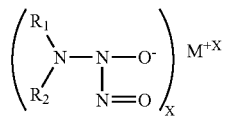

wherein $R_1$ and $R_2$ are independently chosen from straight chain and branched chain $C_1$-$C_{12}$ alkyl groups and benzyl, with the proviso that no branch occur on the alpha carbon atom of the alkyl groups; or $R_1$ and $R_2$ together with the nitrogen atom they are bonded to form a pyrrolidino, piperidino, piperazino or morpholino group, and M+ is a pharmaceutically acceptable cation, wherein X is the valence of the cation.

Further improvements in the control of NO release were achieved when Keefer et al. developed methods for producing novel complexes of NO and polyamines. These compounds were disclosed in U.S. Pat. Nos. 5,155,137 and 5,250,550 and generally provided three general formulae as follows:

Formula 5

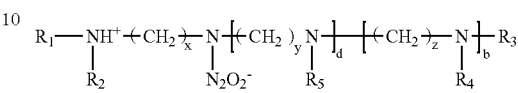

Formula 6

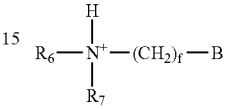

Formula 7

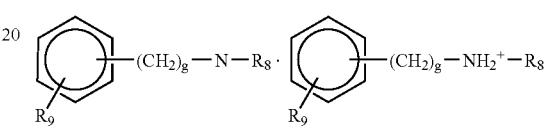

In the above Formulae 5, 6 and 7, b and d are independently zero or one; x, y and z are independently two to twelve; $R_1$ to $R_8$ are independently hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; $R_9$ is hydrogen or a $C_1$-$C_{12}$ straight or branched chain alkyl; B is:

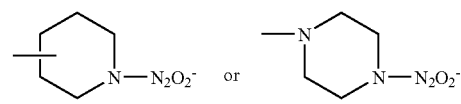

f is zero to twelve, with the proviso that when B is the substituted piperazine moiety

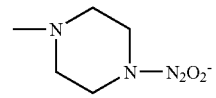

then f is two to twelve; and g is two to six. The group $N_2O_2$— has the structure:

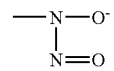

The diazeniumdiolates disclosed in the aforementioned patents each have relative advantages and disadvantages. The primary advantage is that these diazeniumdiolates can be formulated into biocompatible amine containing polymeric compounds. For example, the '919 patent describes biologically acceptable polymers to which NO may be bound including polyolefins, such as polystyrene, polypropylene, polyethylene, polytetrafluoroethylene, polyvinylidene, polyethylenimine, polyesters, polyethers, polyurethanes and the like. The primary disavantages of the polymers described in the '919 patent is that they are typically non- or poorly cross-linked and of low to moderate hydrophobicity. The term "bound" as used herein includes, covalent bonds, ionic bonds, van der Waasl forces, hydrogen bonding, electrostatic bonding and all other methods for attaching NO functional groups such as diazeniumdiolates to polymeric compounds. In addition to polymeric surfaces, the present inventors have also co-developed methods for providing metallic surfaces with covalently bound diazeniumdiolate groups as disclosed in pending U.S. patent application Ser. No. 09/567,579 (the "'579 application") filed May 5, 2000, the entire contents of which are hereby incorporated by reference.

Nitric oxide-releasing diazeniumdiolates of the present invention may be provided to polymers by diazeniumdiolating amine groups within the polymer backbone and/or along pendent groups attached to the polymer backbone or through co-precipitation of the polymer. Moreover, the formation of interpenetrating networks and semi-interpenetrating networks between diazeniumdiolated polymers and or monomers is also contemplated. The polymers of the present invention may also be blended with other polymers such as, but not limited to, polystyrene, polypropylene, polyethylene, polytetrafluoroethylene, polyvinylidene, polyethylenimine, polyesters, polyethers, polyurethanes and the like. More preferably, the polymers of present invention may be extruded as co-polymeric mixtures to form ex vivo medical devices such as, but not limited to, NO-releasing blood collection tubes, storage bags, transdermal patches, wound dressings/bandages, etc. and the like.

For example, thrombocytes are presently stored in standard blood collection bags following their separation from whole blood. However, due to the extreme thermal sensitivity of thrombocytes they must be stored at or just below room temperature. Thrombocytes stored in this manner activate thereby diminishing their therapeutic effectiveness. Consequentially, thrombocyte shelf-life on storage is extremely short. However, thrombocytes maintained in storage bags made from the blended or co-polymerized polymers of the present invention would immediately release NO on contact with the solution bathing the thrombocytes. Consequently, the shelf-life of thrombocytes stored in such bags would be significantly increased while also greatly reducing the potential for microbial growth.

Other embodiments of ex vivo medical devices using the NO-releasing, extremely hydrophobic polymers of the present invention include sutures and wound dressings. These wound management devices can be compounded to include the NO-releasing micro-beads of the present invention. The suture or wound dressings used to seal or cover wounds would release NO directly at the injury site. The NO release rate and duration can be adjusted to promote wound healing and prevent infections.

The polymeric compounds of the present invention, those described in the aforementioned diazeniumdiolate patents and the '579 application are all suited for site specific, in situ NO delivery. Site specific, or localized, NO delivery obviates many of the potentially toxic side effects associated with administering NO systemically. The diazeniumdiolates and polymers of the present invention can be compounded into a variety of medical devices including, but not limited to, stents, catheters, penile implants, condoms, ocular lenses, sling materials, sutures, and the like. These devices can be used to treat or prevent vascular diseases, sexual dysfunction, infections, hypertension, cancer and many other acute and chronic disorders. However, exact, prolonged and highly controllable dosing is required in order to maximize treatment efficacy over such a wide range of diseases using a wide range of medical devices.

Exact dosing, especially over prolonged dosing intervals, has not been perfected for all potential applications using the NO-releasing compounds developed to date. As previously stated, the NONO/polyamine adducts (diazeniumdiolates) of the present invention are highly reactive in physiological conditions. The clean, first order kinetics that make these compounds so useful also contributes to their one main disadvantage. When exposed to hydrogen ion donors such a water or physiological fluids most diazeniumdialoates rapidly break down releasing NO. Consequently, unshielded and unprotected NO groups are generally rapidly depleted resulting in a surge of NO (burst effect) followed by a steadily diminishing rate of NO release. In many instances, NO depletion is complete within minutes to a few hours.

Keefer et al. have reported a wide variety of nitric oxide/nucleophile complexes capable of providing NO in biologically active forms at a semi-predictable rate. These compounds, disclosed in U.S. Pat. No. 5,676,963 (the "'963 patent"), incorporate the diazeniumdiolate groups described above into a wide range of polymeric materials including, but not limited to, polystyrene, polypropylene, polyethylene, polytetrafluoroethylene, polyvinyldene difluoride, polyvinylchloride, polyethyleneimine, polyethers, polyesters, polyamides such as nylon, polyurethanes, biopolymers such as peptides, proteins, oligonucleotides, antibodies and nucleic acids, starburst dendrimers, and the like. The inventors of the '963 patent have postulated that the longevity of the NO release from the polymer bound nitric oxide/nucleophile adducts described therein is attributable in part to the physical structure of the composition and to electrostatic effects. These inventors propose that NONO groups present on the surface of the polymers are released immediately on contact with the physiological medium while those more deeply embedded within the polymer are sterically hindered and require more time and energy to be liberated. Moreover, the inventors of the '963 patent have proposed that protonation of the amine groups in the vicinity of the NONO groups within the polymer exert electrostatic repulsive effects which inhibit hydrogen ion attack on the NONO functional groups.

The polymers of the '963 patent represent a significant advance in controlling NO release from medical grade polymers. However, long lived NO-releasing materials are needed to maximize the benefits of polymeric materials for localized NO release. It was surprisingly discovered that it is possible to design polymers that permit control over the rate and duration of NO release. This is achieved by controlling the polymers' hydrophobicity, extent and degree of cross-linking, thickness, and pore size of the final polymer using the teachings known to those skilled in the art.

The NO-releasing materials of the present invention are composed of polymers containing highly cross-linked, extremely hydrophobic backbones with polydiazeniumdiolated polyamines attached thereto. Such highly cross-linked, extremely hydrophobic polymers are defined as macromolecules composed of an indefinite number of monomers that are highly resistant to penetration by water and insoluble therein. Monomers suitable for forming the highly cross-linked, extremely hydrophobic polymeric materials of the present invention most preferably include, but are not limited to, divinylbenzene and substituted derivatives thereof. Other polymers suitable for forming useful materials of the present invention include blends or co-polymers such as, but not limited to, polyvinylchloride, polystyrene, poly-L-lactides/glycolides, polycaprolactone, polyglycols, silicones, polypropylene, polyethylene, polytetrafluoroethylene, polyvinylidene, polyethylenimine, polyesters, polycarbonates, polyethers, polylactones, polyvinyl acetate, polystyrene, poly(ethylene terephthalate), polyurea, polyamides, natural rubbers, polyurethanes, hydroxymethyl cellulose, hydroxyethyl cellulose, hydroxypropylethyl cellulose, sodium carboxymethyl cellulose, dextran as well as copolymers and combinations.

The NO-releasing diazeniumdiolate groups of the present invention are formed from polyamine pendent groups attached to the highly cross-linked, extremely hydrophobic backbone of the polymer. Most preferably such polyamine groups include, but are not limited to, polyethyleneimine, piperazine and derivatives thereof. In one embodiment of the present invention the polyamine pendent group is pentaethylene hexamine. In another embodiment of the present invention the polyamine group is a derivative of piperazine.

The basic polyamine-derivatized hydrophobic polymer backbone of one embodiment of the present invention is depicted below:

Formula 8

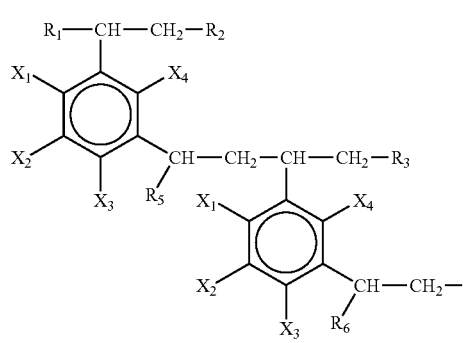

Wherein $R_1$ through $R_4$ are the same or different and may be H, phenyl, benzyl, vinylbenzene, divinylbenzene, un-substituted and substituted alkyl and substituted and un-substituted aryl groups, $X_{1-4}$ are same or different and are H, a halogen, an un-substituted or substituted alkyl and substituted and un-substituted aryl groups providing that the resulting polymeric backbone remains hydrophobic and wherein at least one of $R_5$ and $R_6$ is:

Formula 9

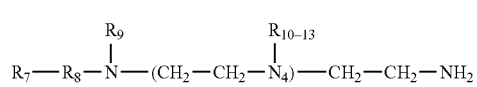

Wherein $R_7$ is a hydrophobic polymeric backbone in accordance with the teachings of the present invention, $R_8$ may be nothing or a $C_{1-12}$ unbranched or branched alkyl group and $R_{9-13}$ may be H, $H_2^+$ or $N_2O_2^-$, $N_2O_2^{-+}NH_2R$, $N_2O_2^{-+}N_2R_2$, $N_2O_2^{-+}NR_3$, $N_2O_2X$; wherein X is methoxymethyl or other suitable protecting group as specified in (Greene, T. W. et al. Protecting groups in organic synthesis; J. Wiley & Sons: New York, 1999, the entire contents of which is hereby incorporated by reference) and providing that at least one of $R_{9-13}$ is $N_2O_2^-$.

Generally, the polyamine derivatized highly cross-linked, extremely hydrophobic polymers of the present invention are diazeniumdiolated using methods known to those skilled in the art and as published in U.S. Pat. Nos. 5,155,157, 5,250,550 and 5,405,919. The basic reaction is depicted below:

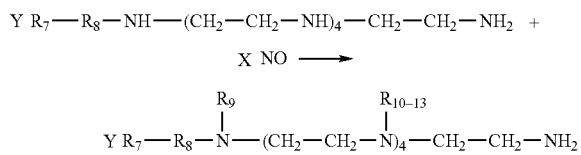

Wherein X is at least 2 and Y is an integer equal to or greater than 1, providing that Y is never greater than X, $R_7$ is a hydrophobic polymeric backbone in accordance with the teachings of the present invention, $R_8$ may be nothing or a $C_{1-12}$ unbranched or branched alkyl group and $R_{9-13}$ may be H or $N_2O_2$— providing that at least one of $R_{9-13}$ is $N_2O_2^-$.

It has been surprisingly discovered that the NO-release rates can be regulated by closely controlling the geometric configuration and monomer cross-linking of the final polyamine-derivatized polymeric backbone. Suitable geometric configurations include, but are not limited to, microbeads ranging in size from 0.5 µm to 100 µm in diameter, amorphous polymeric compounds and polymers compounds cast into specific shapes. In another embodiment of the present invention the polymers have pores ranging in size from 1 nm to 100 nm. The geometry and pore size associated with the hydrophobic amino-derivatized polymers of the present invention are achieved using procedures known to those skilled in the art and as described in: Jordi, H. 1999. Jordi Gel Columns for Size Exclusion Chromatography. In: Column Handbook for Size Exclusion Chromatography. Academic Press: New York, pages 367-425, the entire contents of which are hereby incorporated by reference. The basic chemistry will be described below merely as a convenience to the reader. It is understood that persons of ordinary skill in the polymer arts would be able to produce the highly cross-linked, extremely hydrophobic polyamine-derivatized polymers of the present invention without the aid of the following description. In one embodiment, the microbeads have pores ranging in size from approximately 5 to 500,000 angstrom. In another embodiment, the amorphous masses have pores ranging in size from approximately 5 to 500,000 angstrom.

A suitable purified hydrophobic monomer, such as but not limited to, divinylbenzene, is suspended as a dispersion of small droplets in a continuous phase of water and polymerized by free radical initiation using methods known to those skilled in the art. These processes result in the formation of spherically shaped non-porous beads. Porous beads are made in essentially the same manner except that one or more inert solvents is added to the monomer/water mixture. The solvent used will ultimately control pore size. For polymer beads having relatively small pores solvents are selected in which both the monomer and the forming polymer are soluble. Non-limiting examples of solvents used to generate small-pore polydivinylbenzene beads ranging from 0.5 m to 1 m include, but are not limited to, toluene, ethylbenzene, diethyl benzene and others. For polydivinylbenzene beads having larger pores suitable solvents include, but are not limited to, isooctane, 1- or 2-butanol and t-amyl alcohol.

Once the polymers of the present invention have been made, they may be provided with reactive secondary amines. Briefly, the polymer beads are halogenated using bromine followed by chlorosulfonic acid using reaction conditions known to those of ordinary skill in the art. Next the halogenated polymer is reacted with a suitable polyamine such as, but not limited to, polyethyleneimine. The polyamine derivatized-polymers of the present invention can then be polydiazeniumdiolated as discussed above. In one embodiment of the present invention, the diazeniumdiolate groups form preferentially on secondary amines. The degree of polydiazeniumdiolation is controlled by the solvent system used to form the diazeniumdiolate salts. When a pure organic solvent such as acetonitrile is used to suspend the polyamine-derivatized polymer during the diazeniumdiolation procedure, every other secondary amine is converted into a diazeniumdiolate group. The alternating secondary amines form ammonium cations resulting in stable zwitterions. However, when a cation containing solvent such as, but not limited to, sodium methylate is used, diazeniumdiolate groups can form on every available secondary amine resulting in stable, sodium polydiazeniumdiolate salts on the polymer.

Nitric oxide release from the polydiazeniumdiolated polymers of the present invention is regulated by the combined effects of cross-linking, pore size and the hydrophobic nature of the polymer. It will be recognized by those of skill in the art that the polymeric compounds of the present invention are significantly different from those disclosed in the U.S. Pat. Nos. 4,954,526, 5,039,705, 5,155,137, 5,212,204, 5,250,550, 5,366,997, 5,405,919, 5,525,357, 5,650,447 and 5,676,963 all issued to Keefer and Keefer et al (referred to collectively hereinafter as the "Keefer" patents). Unlike compounds in these earlier Keefer patents, the polymers of the present invention are highly cross-linked. Cross-linking improves the structural rigidity and chemical stability of a given polymer.

The term "highly cross-linked" as used herein is consistent with its ordinary meaning as understood by persons skilled in the art of synthetic organic chemistry. Therefore, as used in the present invention, the term "highly cross-linked" is defined as a polymer substrate having an extensive network of primary chemical bonds linking the individual monomers together such that the polymer is essentially bound into a single molecule. This definition is not inconsistent with the general understanding of the "highly-cross-linked." For example, and not intended as a limitation, when divinylbenzene (DVB) is used to form the polymer beads of the present invention, the individual monomers of DVB become linked together (polymerized) by interactions between vinyl groups on neighboring DVB molecules. As the polymer chain grows additional polymerization reactions occur within the polymer chain resulting in a cross-linked matrix. The more extensive these additional interactions are, the more highly cross-linked the polymer becomes.

The extreme hydrophobicity of its divinylbenzene substituents prevents such a polymer from swelling when immersed in aqueous solutions such as physiological or bodily fluids. While not wishing to be bound by any particular theory, it is believed that in non- or poorly cross-linked diazeniumdiolated hydrophobic polymers of the type disclosed in the prior art and in the '919 patent, the intrusion of water and other protonating species into the interior of the polymer causes it to rapidly swell. As large hydrophilic channels are created, the protonation of sequestered diazeniumdiolate groups within the polymer is facilitated and there is a corresponding liberation of NO from the polymer.

This process contrasts with that of the highly cross-linked, extremely hydrophilic cross-linked polymers of the present invention. Such polymers do not swell appreciably upon immersion in physiological solutions or bodily fluids; moreover, the extremely hydrophobic character of such polymers significantly restricts the ability of water molecules to penetrate the polymer's interior, as a result NO release can be sustained for significantly longer time periods than those described in the prior art. The ability to control the presence or absence of pores as well as pore sizes provides an additional means of optimizing NO release from the polymer for a given application. For example, larger pores permit more water to reach the diazeniumdiolate groups in the polymer's interior while also providing enhanced pathways for the egress of NO. Therefore, the larger the pore, the greater the amount of NO that will be released per unit time and the shorter the duration of total NO release for a standardized NO load is likely to be. This degree of flexibility in NO-releasing polymer design has never before been demonstrated and makes possible precise localized dosing and metering of NO use in conjunction with medical devices.

The NO-releasing polydiazeniumdiolated polymers of the present invention generate between approximately 0.2 µmoles and 2.0 µmoles/mg of polymer. These values represent a 100 to 1000-fold increase over the amounts of NO generated by the polymers of the '919 patent. Moreover, the NO-releasing polymers of the present invention have the potential to continually release NO for up to nine (9) months or more. This far exceeds any previously reported NO release rates or duration. For example, Bauer et al. report polyethyleneimine/nitric oxide adducts that released 0.2 µmoles/mg of NO for a maximum duration of sixty (60) hours (J. A. Bauer, et al. 1998. Evaluation of Linear Polyethyleneimine/nitric oxide adducts on wound repair: therapy versus toxicity. Wound Repair and Regeneration. November-December: 569-576). In another recently reported study, Mowery et al. reported polydiazeniumdiolated hydrophobic polymers whose release of NO was measured in days rather than months as in the present invention (K. A. Mowery et al. 2000. Preparation and characterization of hydrophobic polymeric films that are thromboresistant via nitric oxide release. Biomaterials. 21:9-21). Moreover, the hydrophobic polymers of Mowery et al. were not highly cross-linked nor do they exhibit the extreme degree of hydrophobicity, control over pore size and chemical stability as polymers in the present invention.

The Keefer patents report polydiazeniumdiolated polymers having a wide range of NO release rates and capacities. For example, U.S. Pat. Nos. 5,650,447, 5,676,963, and 5,718,892 report NO-releasing polymers having total NO generation capacities ranging from 3 to 11 nmoles/mg with NO release half-lives measured in minutes to hours. The polymers disclosed in these patents tend to be hydrophilic and non- or poorly cross-linked.

Furthermore, while not wishing to be bound by any particular theory, the inventors believe that the increased NO loading capacity and sustained release rate of the polymers in the present invention is a multi-factorial phenomenon that includes polymer thickness, pore size, hydrophobicity, and degree and extent of cross-linking, and the type and number of secondary amine sites present on the polyamine substituent. In one embodiment of the present invention bead-shaped polymers are formed that are then diazeniumdiolated. In another embodiment of the present invention extensively cross-linked, polyethyleneimine derivatized divinylbenzenes are formed having amorphous matrices of varying thickness, hydrophobicity, and pore size. The resulting polymer's porosity plays a significant role in NO release in aqueous solutions such as physiological or bodily fluids. For example, highly cross-linked, extremely hydrophobic polymers of the present invention lacking pores do not exhibit an NO "burst" phase when exposed to aqueous protonating conditions. Rather, poreless highly cross-linked, extremely hydrophobic polymers of the present invention release NO at a steady rate comparable to that at which porous beads release NO following their initial NO burst phase.

The inventors further proposed a non-limiting theory to partially explain the characteristic NO release profiles of the present invention. The high degree of cross-linking and extreme hydrophobicity present in nonporous polymers greatly restricts the ability of polar solvents like water to readily penetrate the polymer's surface. As a result, in nonporous polymers of the present invention, diazeniumdiolate groups lying just below the polymer's surface are not rapidly protonated and NO is slowly evolved from such polymers without a rapid or "burst" phase of release. In contrast, polymers containing pores which vary in diameter from 100 to 100,000 Å allow water molecules to access a much higher proportion of polymer's surface area. Diazeniumdiolate groups residing near or just below the polymer's surface are rapidly protonated and there is a corresponding "burst" or rapid phase of NO release whenever these polymers come into contact with protonating physiological solutions or bodily fluids.

The following non-limiting examples offer four methods for the preparation of the polydiazeniumdiolated highly cross-linked, extremely hydrophobic polymers of the present invention. It is understood that using skills known to those in the art of polymer chemistry, many other embodiments of the present invention can be prepared in accordance with the teachings described herein.

EXAMPLES

Example 1

Polydiazeniumdiolation of Pentaethylene Hexamine-Derivatized Polydivinyl Benzene Micro-Beads using Acetonitrile (size: 5 µm, porosity: 100 Å)

In a 50 ml Parr® hydrogenation bottle was added 250 mg of pentaethylene hexamine-derivatized polydivinylbenzene micro-beads (size 5 µm, porosity: 100 Å) and 10 ml of acetonitrile. The bottle was attached to a NO apparatus and degassed by repeated cycles (×10) of pressurization/depressurization with $N_2$ at 4 atmospheres. Next, the bottle was pressurized/depressurized with repeated cycles (×10) of NO at 4 atmospheres. The vessel was then filled with NO at 4 atmospheres and stirred at room temperature for 48 hrs. After 48 hrs. the bottle was purged of NO and pressurized/depressurized with repeated cycles (×10) of $N_2$ at 4 atmospheres. The acetonitrile suspension of polydiazeniumdiolated pentaethylene hexamine-derivatized polydivinylbenzene micro-beads (size 5 µm, porosity: 100 Å) was then transferred to a 12 ml test tube and centrifuged in a Dynac® table top centrifuge at 5,000 RPM for 7 min. The filtrate was decanted, 10 ml of acetonitrile was added and the pellet was resuspended using a vortex mixer. Two additional cycles of centrifugation-decantation-resuspension were conducted in acetonitrile and diethyl ether. The procedure resulted in a solvent wet pellet of the substituted ammonium form of polydiazeniumdiolated pentaethylene hexamine-derivatized polydivinylbenzene micro-beads at the bottom of the test tube. The pellet was dried by placing the micro-beads under a stream of nitrogen gas for 10 min.

A 21.05 mg sample of the dry micro-beads was immersed in phosphate buffer, pH 7.4 at 37° C., whereupon chemiluminescence-detectable NO evolved during a 138-day period of analysis. The total NO released was measured at $6.21 \times 10^{-6}$ mole or 0.18 µmole/mg. By carefully plotting the measured data from the initial 138-day period of NO release and extrapolating this curve into the future, it is estimated that NO-release from the micro-beads will continue for another 160 days (or approximately 9.8 months of continuous NO release).

Example 2

Diazeniumdiolation of Pentaethylene Hexamine-Derivatized Polydivinyl Benzene Micro-Beads using a 6% Sodium Methylate Solution (size: 5 µm, porosity: 100 Å)

In a 15 ml pear-shaped flask was added 300 mg of pentaethylene hexamine-derivatized polydivinylbenzene micro-beads (size 5 µm, porosity: 100 Å) and 10 ml of a 6% sodium methylate solution. The flask was placed in a Series 4751 Parr® pressure vessel and degassed by repeated cycles (×10) of pressurization/depressurization with $N_2$ at 10 atmospheres. Next, the vessel was pressurized/depressurized with repeated cycles (×3) of NO at 30 atmospheres. The vessel was then filled with NO at 30 atmospheres and stirred at room temperature for 48 hrs. After 48 hrs, the vessel was purged of NO and pressurized/depressurized with repeated cycles (×10) of $N_2$ at 10 atmospheres. The flask containing the polydiazeniumdiolated pentaethylene hexamine-derivatized polydivinylbenzene micro-beads (size 5 µm, porosity: 100 Å) was then removed from the vessel. The suspended micro-beads were then transferred to a 12 ml test tube and centrifuged in a Dynac® table top centrifuge at 5,000 RPM for 7 min. The filtrate was decanted, 10 ml of methanol was added and the pellet was resuspended using a vortex mixer. Two additional cycles of centrifugation-decantation-resuspension were conducted in methanol and diethyl ether. The procedure resulted in a solvent wet pellet of the sodium salt of polydiazeniumdiolated pentaethylene hexamine-derivatized polydivinylbenzene micro-beads at the bottom of the test tube. The pellet was dried by placing the micro-beads under a stream of nitrogen gas for 10 min.

A 0.15 mg sample of the dry micro-beads was immersed in phosphate buffer, pH 7.4 at 37° C., whereupon chemiluminescence-detectable NO evolved during a 57-day period of analysis. The total NO released was measured at $2.73 \times 10^{-7}$ mole or 1.85 µmole/mg. By carefully plotting the measured data from the initial 57-day period of NO release and extrapolating this curve into the future, it is estimated that NO-release from the micro-beads will continue for another 280 days (or approximately 10.8 months of continuous NO release).

Example 3

A Polymeric Blend Comprised of the Sodium Salt of Polydiazeniumdiolated Pentaethylene Hexamine-Derivatized Polydivinyl Benzene Micro-Beads (size: 5 µm, porosity: 100 Å) and Polyvinylchloride In a KBr press was added 200 mg of polyvinyl chloride and 20 mg of the sodium salt of polydiazeniumdiolated pentaethylene hexamine-derivatized polydivinylbenzene (described in Example 2) and pressed using a hydraulic press to 12,000 psi. The resulting fragile pellet was placed on watch glass and cover with tetrahydrofuran. The solvent was allowed to slowly evaporate on the edge of a laboratory fume hood. The pellet which remained was briefly dried in vacuo and evaluated for its ability to release NO.

A sample consisting of approximately 25 percent of the pellet (0.51 mg) was immersed in phosphate buffer, pH 7.4 at 37° C., whereupon chemiluminescence-detectable NO evolved during a 14-day period of analysis. The total NO released was measured at $6.23 \times 10^{-7}$ mole or 0.12 µmole/mg. By carefully plotting the measured data from the initial 4-day period of NO release and extrapolating this curve into the future, it is estimated that NO-release from the micro-beads will continue for another 10 days.

Example 4

Poly (methoxymethyl monodiazeniumdiolated) Derivative of Piperazine Derivatized Polydivinyl Benzene Micro-Beads (size: 5 µm, porosity: 100 Å)

In a 15 ml pear shaped vessel were added 50 mg of brominated polydivinylbenzene micro-beads, 2.0 g of $O^2$-methoxymethyl 1-(piperazin-1-yl)diazen-1-ium-1,2-diolate and 5 ml of tetrahydrofuran (THF). The mixture was heated to reflux under nitrogen gas stirred overnight. The next morning a dense precipitate had formed which was suspended in THF in a 12 ml test tube and centrifuged in a Dynac® table top centrifuge at 5,000 RPM for 7 min. The filtrate was decanted, 10 ml of methanol added and the pellet was resuspended using a vortex mixer. Four additional cycles of centrifugation-decantation-resuspension were conducted in methanol and diethyl ether. This procedure resulted in a solvent wet pellet of the poly(methoxymethyl monodiazeniumdiolated) derivative of piperazine derivatized polydivinylbenzene micro-beads at the bottom of the test tube. The pellet was taken to dryness under a stream of nitrogen gas for 10 min resulting in 74 mg of product.

A 1.5 mg sample of the dry micro-beads was immersed in phosphate buffer, pH 7.4 at 37° C., whereupon chemiluminescence-detectable NO evolved during a 5-day period of analysis. The total NO released was measured at $3.12 \times 10^{-8}$ mole or 0.021 µmole/mg. By carefully plotting the measured data from the initial 5-day period of NO release and extrapolating this curve into the future, it is estimated that NO-release from the micro-beads will continue for another 7 days.

Nitric oxide analysis was performed using a nitric oxide analyzer and was patterned after the procedure of Maragos, et al. 1991. J. Med. Chem., 34 3242-3247 (the entire contents of which is hereby incorporated by reference). Briefly, a reactor vessel fitted with a septum is charged with a small quantity of test polymer and the system is purged of oxygen using helium gas. The reaction is initiated by injecting 2 ml of 0.1 M sodium phosphate buffer, pH 7.4 through the vessel septum. The NO-containing gaseous effluent is swept away and into a chemiluminescence detector (Thermal Energy Analyzer Model 502LC, Thermedics, Inc. Woburn, Mass.). Data are electronically analyzed and compared to known standards.

The highly cross-linked, extremely hydrophobic polyamine derivatized NO-releasing polymers of the present invention can be used in a variety of applications where both short-term and long-term NO release is desired. For example, certain cardiovascular applications may require high NO "bursts" immediately after stent or vascular graft implantation followed by sustained low level NO delivery for weeks to months. Alternatively, there may be applications where continuous NO levels are preferred and a burst effect is undesirable. In these cases, the NO-releasing highly cross-linked, extremely hydrophobic polymers of the present invention can be specifically formulated to achieve these results.

The highly cross-linked, extremely hydrophobic NO-releasing polymers of the present invention are quite versatile and can be used to deliver therapeutic and prophylactic NO levels to any anatomical location. For example, the hydrophobic polymers of the present invention can be co-polymerized or blended with other biocompatible polymers such as, but not limited to, polystyrene, polypropylene, polyethylene, polytetrafluoroethylene, polyvinylidene, polyethylenimine, polyesters, polyethers, polyurethanes and the like. The resulting polymers can then be used to fabricate implantable medical devices ranging from stents for cardiovascular applications to penile implants for the treatment of sexual dysfunction. Moreover, the highly cross-linked, extremely hydrophobic polymers of the present invention can also be formed into micro-beads as previously described. These beads can be injected via a catheter into the coronary arteries. After injection, the NO-releasing micro-beads would migrate into the extremities of the coronary circulation and become lodged at points where the vessel lumen is smaller than the bead's diameter. Nitric oxide would then be released locally from the beads at levels sufficient to induce angiogenesis. The size of the micro-beads would be controlled so as to prevent them from blocking larger arterioles and exacerbating the ischemia resulting from the ongoing stenosis.

The biocompatible highly cross-linked, extremely hydrophobic polymers of the present invention can be used to coat a wide range of medical devices made from a variety of materials including, but not limited to, metals, glass, ceramics, fabrics and polymers. Moreover, the micro-bead embodiment can also be used to fashion prostheses such as porcine and bovine heart valves with NO-releasing surfaces. Consequently, the performance of medical implants and prostheses provided with NO-releasing compounds of the present invention will be greatly enhanced. For example, a medical device, such as but not limited to, a pacemaker can be provided with an NO-releasing surface made from polymers of the present invention. Following implantation, the NO release from such a polymeric coating would help reduce inflammation, promote wound healing and prevent post-implantation infections. As a result, the patient's overall recovery time would be significantly altered. Other expected benefits include a decrease in postoperative side effects, shortened hospitalization, and reduced healthcare related expenses.

We claim:

1. A highly cross-linked, extremely hydrophobic nitric oxide releasing biocompatible polymer wherein said biocompatible polymer is a polyamine derivatized form of polydivinylbenzene having the general formula:

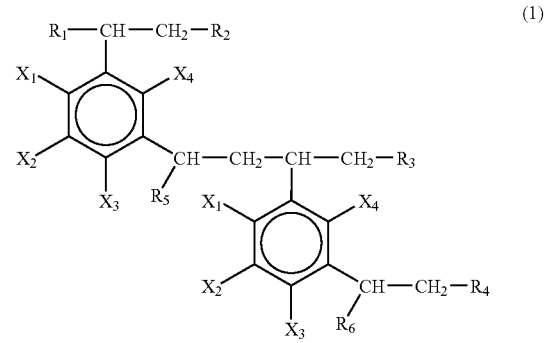

(1)

wherein $R_1$ through $R_4$ are the same or different and may be H, phenyl, benzyl, vinylbenzene, divinylbenzene, un-substituted and substituted alkyl and substituted and un-substituted aryl groups, $X_{1-4}$ are same or different and may be H, a halogen, an un-substituted or substituted alkyl and substituted or unsubstituted aryl groups providing that the resulting polymeric backbone remains hydrophobic and wherein at least one of $R_5$ and $R_6$ is:

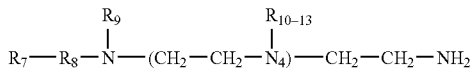

wherein $R_7$ is a hydrophobic polymer backbone, $R_8$ may be nothing or a $C_{1-12}$ unbranched or branched alkyl group and $R_{9-13}$ may be H or $N_2O_2^-$ providing that at least one of $R_{9-13}$ is $N_2O_2^-$; and wherein said biocompatible polymer does not swell upon immersion in an aqueous solution.

2. The highly cross-linked, extremely hydrophobic nitric oxide-releasing biocompatible polymers of claim 1 wherein said polymer forms micro-beads.

3. The highly cross-linked, extremely hydrophobic nitric oxide-releasing biocompatible polymers of claim 1 wherein said polymer forms amorphous masses.

4. The highly cross-linked, extremely hydrophobic nitric oxide-releasing biocompatible polymers of claim 2 wherein said micro-beads have diameters ranging from approximately 1 µm to approximately 100 µm.

5. The highly cross-linked, extremely hydrophobic nitric oxide-releasing biocompatible polymers of claim 2 wherein said micro-beads have pores.

6. The highly cross-linked, extremely hydrophobic nitric oxide-releasing biocompatible polymers of claim 2 wherein said micro-beads have pores ranging in size from approximately 5 to 500,000 Å.

7. The highly cross-linked, extremely hydrophobic nitric oxide-releasing biocompatible polymers of claim 3 wherein said amorphous masses have pores ranging in size from approximately 5 to 500,000 Å.

8. A therapeutic agent comprising the highly cross-linked, extremely hydrophobic nitric oxide-releasing biocompatible polymers of any one of claims 1, 2, 3, 4, 5, 6 and 7.

9. A medical device comprising a highly cross-linked, extremely hydrophobic nitric oxide-releasing biocompatible polymer, said medical device selected from the group consisting of stents, vascular grafts, pacemaker leads, heart valves, electrodes, sensors, trocars, guide wires, catheters, penile implants, condoms, tampons, sanitary napkins, ocular lenses, sling materials, sutures, wound dressings/bandages, blood collection bags and storage tubes, tubing used for blood transfusions and hemodialysis, and the like according to any one of claims 1, 2, 3, 4, 5, 6 and 7.

10. A medical device coating comprising a highly cross-linked, extremely hydrophobic nitric oxide-releasing biocompatible polymer, said medical device selected from the group consisting of stents, vascular grafts, pacemaker leads, heart valves, electrodes, sensors, trocars, guide wires, catheters, penile implants, condoms, tampons, sanitary napkins, ocular lenses, sling materials, sutures, wound dressings/bandages, blood collection bags and storage tubes, tubing used for blood transfusions and hemodialysis, and the like according to any one of claims 1, 2, 3, 4, 5, 6 and 7.

11. A therapeutic agent comprising the highly cross-linked, extremely hydrophobic nitric oxide-releasing biocompatible polydiazeniumdiolated polymers according to any one of claims 1, 2, 3, 4, 5, 6 and 7.

12. A medical device comprising a highly cross-linked, extremely hydrophobic nitric oxide-releasing biocompatible polydiazeniumdiolated polymer, said medical device selected from the group consisting of stents, vascular grafts, pacemaker leads, heart valves, electrodes, sensors, trocars, guide wires, catheters, penile implants, condoms, tampons, sanitary napkins, ocular lenses, sling materials, sutures, wound dressings/bandages, blood collection bags and storage tubes, tubing used for blood transfusions and hemodialysis, and the like according to any one of claims 1, 2, 3, 4, 5, 6 and 7.

13. A medical device coating comprising a highly cross-linked, extremely hydrophobic nitric oxide-releasing biocompatible polydiazeniumdiolated polymer, said medical device selected from the group consisting of stents, vascular grafts, pacemaker leads, heart valves, electrodes, sensors, trocars, guide wires, catheters, penile implants, condoms, tampons, sanitary napkins, ocular lenses, sling materials, sutures, wound dressings/bandages, blood collection bags and storage tubes, tubing used for blood transfusions and hemodialysis, and the like according to any one of claims 1, 2, 3, 4, 5, 6 and 7.

* * * * *

UNITED STATES PATENT AND TRADEMARK OFFICE
CERTIFICATE OF CORRECTION

PATENT NO. : 7,226,586 B2
APPLICATION NO. : 10/623239
DATED : June 5, 2007
INVENTOR(S) : Fitzhugh et al.

It is certified that error appears in the above-identified patent and that said Letters Patent is hereby corrected as shown below:

Column 19, line 4,

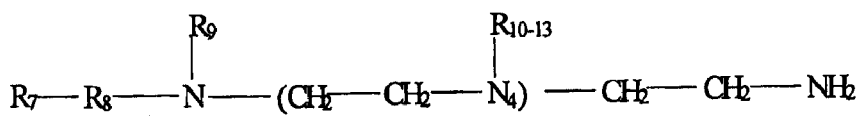

should be changed to:

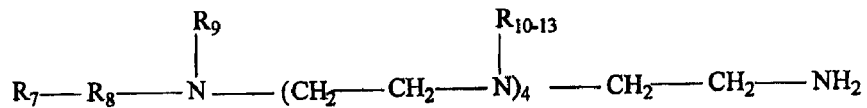

Signed and Sealed this

Eleventh Day of November, 2008

JON W. DUDAS
*Director of the United States Patent and Trademark Office*